(12) United States Patent
Labourdette et al.

(10) Patent No.: US 10,349,658 B2
(45) Date of Patent: Jul. 16, 2019

(54) METHOD FOR TREATING COFFEE RUST, CITRUS BLACK SPOT, CITRUS SCAB AND BANANA BLACK SIGATOKA DISEASES

(71) Applicant: Bayer CropScience Aktiengesellschaft, Monheim am Rhein (DE)

(72) Inventors: Gilbert Labourdette, Paray le Monial (FR); Rodrigo Guerzoni, Americana /SP (BR)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/575,298

(22) PCT Filed: May 18, 2016

(86) PCT No.: PCT/EP2016/061064
§ 371 (c)(1),
(2) Date: Nov. 17, 2017

(87) PCT Pub. No.: WO2016/184879
PCT Pub. Date: Nov. 24, 2016

(65) Prior Publication Data
US 2018/0153169 A1 Jun. 7, 2018

(30) Foreign Application Priority Data
May 19, 2015 (EP) .................... 15290131

(51) Int. Cl.
*A01N 43/56* (2006.01)
*A01N 53/00* (2006.01)

(52) U.S. Cl.
CPC ............ *A01N 43/56* (2013.01); *A01N 53/00* (2013.01)

(58) Field of Classification Search
CPC ................................ A01N 43/56; A01N 53/00
See application file for complete search history.

(56) References Cited

U.S. PATENT DOCUMENTS

| | | | |
|---|---|---|---|
| 8,765,636 B2* | 7/2014 | Dahmen | A01N 37/22 504/100 |
| 8,772,266 B2* | 7/2014 | Bartels | C07D 231/16 514/63 |
| 9,668,480 B2* | 6/2017 | Cristau | A01N 55/00 |
| 9,801,374 B2* | 10/2017 | Cristau | A01N 57/20 |
| 2014/0038823 A1* | 2/2014 | Dahmen | A01N 43/56 504/103 |
| 2017/0347651 A1* | 12/2017 | Dahmen | A01N 37/50 |

* cited by examiner

*Primary Examiner* — My-Chau T. Tran
(74) *Attorney, Agent, or Firm* — Morrison & Foerster LLP

(57) ABSTRACT

The invention relates to the use of a compound of formula (I) or salts thereof for controlling coffee rust, *citrus* black spot, *citrus* scab or banana black sigatoka disease, and to corresponding methods.

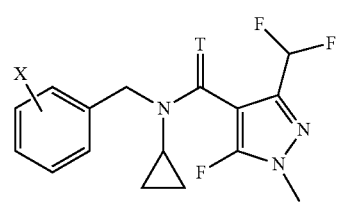

(I)

4 Claims, No Drawings

METHOD FOR TREATING COFFEE RUST, CITRUS BLACK SPOT, CITRUS SCAB AND BANANA BLACK SIGATOKA DISEASES

CROSS REFERENCE TO RELATED APPLICATIONS

This application is the national stage of International Application No. PCT/EP2016/061064, filed internationally on May 18, 2016, which claims the benefit of European Application No. 15290131.0, filed May 19, 2015.

The invention relates to the use of N-cyclopropyl-N-[substituted-benzyl]-3-(difluoromethyl)-5-fluoro-1-methyl-1H-pyrazole-4-carboxamide or thiocarboxamide derivatives and/or salts thereof for the control of phytopathogenic fungi of coffee, *citrus* and banana.

N-cyclopropyl-N-[substituted-benzyl]-3-(difluoromethyl)-5-fluoro-1-methyl-1H-pyrazole-4-carboxamide or thiocarboxamide derivatives, their preparation from commercially available materials and their use as fungicides are disclosed in WO2007/087906, WO2009/016220, WO2010/130767 and EP2251331. It is also known that these compounds can be used as fungicides and mixed with other fungicides or insecticides (cf. patent applications PCT/EP2012/001676 and PCT/EP2012/001674).

Nevertheless, there is no explicit disclosure or suggestion that said compounds may significatively control main phytopathogenic fungi of coffee, *citrus* and banana, and in particular coffee rust, *citrus* black spot, *citrus* scab and banana black sigatoka diseases.

Coffee rust caused by the fungus *Hemileia vastatrix* is the most devastating disease of coffee plants. The symptoms of coffee rust include small, yellowish, oily spots on the upper leaf surface that expand into larger round spots that turn bright orange to red and finally brown with a yellow border. The rust pustules are powdery and orange-yellow on the underleaf surface. Later the pustules turn black. Rusted leaves drop so that affected trees are virtually denuded. Such trees usually die within a few years.

Citrus Black Spot caused by the fungus *Guignardia citricarpa* is a fungal disease which is responsible to a reduction in both fruit quantity and quality. Symptoms include both fruit and leaf lesions, the latter being critical to inter-tree dispersal.

*Elsinoe fawcettii* (and its anamorph *Sphaceloma fawcettii*) is a pathogen that causes scab lesions on *citrus* fruit, leaves, and twigs. *E. fawcettii* affects many different varieties of *citrus*. It has a distinctive morphology from other species in its genus and it is economically significant in any wet, tropical or subtropical climates where *citrus* is grown.

Black Sigatoka, also known as black leaf streak and caused by the fungus *Mycosphaerella fijiensis*, is a very damaging and difficult to control disease. It causes significant reductions in leaf area, yield losses of 50% or more, and premature ripening.

It was therefore an object of the present invention to provide further compounds which increase the control of coffee rust, *citrus* black spot, *citrus* scab or banana black sigatoka diseases.

The present invention accordingly provides for the use of a compound having the formula (I)

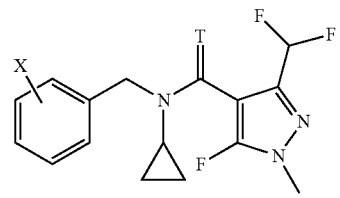

wherein T represents an oxygen or a sulfur atom and X is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro-6-(trifluoromethyl), 3-chloro-2-fluoro-6-(trifluoromethyl) and 2-ethyl-4,5-dimethyl, or an agrochemically acceptable salt thereof, for controlling coffee rust, *citrus* black spot, *citrus* scab or banana black sigatoka disease.

The invention further relates to a method for treating plants in need of control of coffee rust, *citrus* black spot, *citrus* scab or banana black sigatoka disease, comprising applying to said plants or parts of said plants, including leaves and fruits, to seeds from which they grow or to the locus in which they grow, an effective amount for controlling the disease, of a compound according to formula (I)

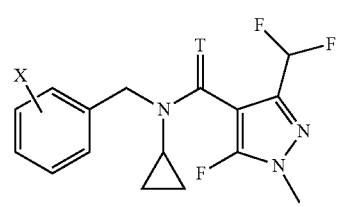

wherein T represents an oxygen or a sulfur atom and X is selected from the list of 2-isopropyl, 2-cyclopropyl, 2-tert-butyl, 5-chloro-2-ethyl, 5-chloro-2-isopropyl, 2-ethyl-5-fluoro, 5-fluoro-2-isopropyl, 2-cyclopropyl-5-fluoro, 2-cyclopentyl-5-fluoro, 2-fluoro-6-isopropyl, 2-ethyl-5-methyl, 2-isopropyl-5-methyl, 2-cyclopropyl-5-methyl, 2-tert-butyl-5-methyl, 5-chloro-2-(trifluoromethyl), 5-methyl-2-(trifluoromethyl), 2-chloro-6-(trifluoromethyl), 3-chloro-2-fluoro-6-(trifluoromethyl) and 2-ethyl-4,5-dimethyl, or an agrochemically acceptable salt thereof.

In the context of the invention, coffee means any trees or shrubs of the genus *Coffea*, particularly tropical and especially *C. Arabica* or *C. canephora*.

In the context of the invention, *citrus* means any trees or shrubs of the rutaceous genus *Citrus*, particularly tropical and subtropical. It includes in particular the orange, lemon, lime, grapefruit, citron, calamondin.

In the context of the invention, banana means any herbaceous treelike plants of the musaceous genus *Musa*, particularly tropical and subtropical, and especially *M. sapientum*.

In particular embodiments of the uses and methods of the present invention, coffee rust is caused by a fungus from *Hemileia* sp., particularly *Hemileia vastatrix*.

In particular embodiments of the uses and methods of the present invention, *citrus* black spot rust is caused by a fungus from *Guignardia* sp., particularly *Guignardia citricarpa*.

In particular embodiments of the uses and methods of the present invention, citrus scab is caused by a fungus from *Elsinoe* sp., particularly *Elsinoe fawcettii*.

In particular embodiments of the uses and methods of the present invention, banana black sigatoka disease is caused by a fungus from *Mycosphaerella* sp., particularly *Mycosphaerella fijiensis*.

Preference is given to the use and method according to the invention wherein the compound of the formula (I) is selected from the group consisting of:

N-cyclopropyl-3-(difluoromethyl)-5-fluoro-N-(2-isopropylbenzyl)-1-methyl-1H-pyrazole-4-carboxamide (compound A1), N-cyclopropyl-N-(2-cyclopropylbenzyl)-3-(difluoromethyl)-5-fluoro-1-methyl-1H-pyrazole-4-carboxamide (compound A2), N-(2-tert-butylbenzyl)-N-cyclopropyl-3-(difluoromethyl)-5-fluoro-1-methyl-1H-pyrazole-4-carboxamide (compound A3), N-(5-chloro-2-ethylbenzyl)-N-cyclopropyl-3-(difluoromethyl)-5-fluoro-1-methyl-1H-pyrazole-4-carboxamide (compound A4), N-(5-chloro-2-isopropylbenzyl)-N-cyclopropyl-3-(difluoromethyl)-5-fluoro-1-methyl-1H-pyrazole-4-carboxamide (compound A5), N-cyclopropyl-3-(difluoromethyl)-N-(2-ethyl-5-fluorobenzyl)-5-fluoro-1-methyl-1H-pyrazole-4-carboxamide (compound A6), N-cyclopropyl-3-(difluoromethyl)-5-fluoro-N-(5-fluoro-2-isopropylbenzyl)-1-methyl-1H-pyrazole-4-carboxamide (compound A7), N-cyclopropyl-N-(2-cyclopropyl-5-fluorobenzyl)-3-(difluoromethyl)-5-fluoro-1-methyl-1H-pyrazole-4-carboxamide (compound A8), N-(2-cyclopentyl-5-fluorobenzyl)-N-cyclopropyl-3-(difluoromethyl)-5-fluoro-1-methyl-1H-pyrazole-4-carboxamide (compound A9), N-cyclopropyl-3-(difluoromethyl)-5-fluoro-N-(2-fluoro-6-isopropylbenzyl)-1-methyl-1H-pyrazole-4-carboxamide (compound A10), N-cyclopropyl-3-(difluoromethyl)-N-(2-ethyl-5-methylbenzyl)-5-fluoro-1-methyl-1H-pyrazole-4-carboxamide (compound A11), N-cyclopropyl-3-(difluoromethyl)-5-fluoro-N-(2-isopropyl-5-methylbenzyl)-1-methyl-1H-pyrazole-4-carboxamide (compound A12), N-cyclopropyl-N-(2-cyclopropyl-5-methylbenzyl)-3-(difluoromethyl)-5-fluoro-1-methyl-1H-pyrazole-4-carboxamide (compound A13), N-(2-tert-butyl-5-methylbenzyl)-N-cyclopropyl-3-(difluoromethyl)-5-fluoro-1-methyl-1H-pyrazole-4-carboxamide (compound A14), N-[5-chloro-2-(trifluoromethyl)benzyl]-N-cyclopropyl-3-(difluoromethyl)-5-fluoro-1-methyl-1H-pyrazole-4-carboxamide (compound A15), N-cyclopropyl-3-(difluoromethyl)-5-fluoro-1-methyl-N-[5-methyl-2-(trifluoromethyl)benzyl]-1H-pyrazole-4-carboxamide (compound A16), N-[2-chloro-6-(trifluoromethyl)benzyl]-N-cyclopropyl-3-(difluoromethyl)-5-fluoro-1-methyl-1H-pyrazole-4-carboxamide (compound A17), N-[3-chloro-2-fluoro-6-(trifluoromethyl)benzyl]-N-cyclopropyl-3-(difluoromethyl)-5-fluoro-1-methyl-1H-pyrazole-4-carboxamide (compound A18), N-cyclopropyl-3-(difluoromethyl)-N-(2-ethyl-4,5-dimethylbenzyl)-5-fluoro-1-methyl-1H-pyrazole-4-carboxamide (compound A19), and N-cyclopropyl-3-(difluoromethyl)-5-fluoro-N-(2-isopropylbenzyl)-1-methyl-1H-pyrazole-4-carbothio-amide (compound A20), or an agrochemically acceptable salt thereof.

More preferred compound of formula (I) is N-(5-chloro-2-isopropylbenzyl)-N-cyclopropyl-3-(difluoromethyl)-5-fluoro-1-methyl-1H-pyrazole-4-carboxamide (compound A5).

The present invention accordingly provides for the use of at least one compound of formula (I) as herein defined or salts thereof, or of any desired mixtures of compound of formula (I) as herein defined or salts thereof with active agrochemical ingredients in accordance with the definition below, and to method using said compound, mixtures or salts, for enhancing the control of coffee rust, *citrus* black spot, *citrus* scab or banana black sigatoka disease.

The present invention further provides a spray solution for treatment of plants, comprising an amount, effective for controlling coffee rust, *citrus* black spot, *citrus* scab or banana black sigatoka disease, of at least one compound of formula (I) as herein defined or salts thereof.

In one embodiment, it is possible, for example, that at least one compound of formula (I) as herein defined or salts thereof is applied by spray application to appropriate plants or plant parts to be treated. The use of at least one compound of formula (I) as herein defined or salts thereof envisaged in accordance with the invention is effected preferably with a dosage between 0.0005 and 3 kg/ha, more preferably between 0.001 and 2 kg/ha, especially preferably between 0.001 and 1 kg/ha. When, in the context of the present invention, abscisic acid is used simultaneously with at least one compound of formula (I) as herein defined or salts thereof, for example in the context of a joint preparation or formulation, abscisic acid is preferably added in a dosage between 0.001 and 3 kg/ha, more preferably between 0.001 and 2 kg/ha, especially preferably between 0.001 and 1 kg/ha.

More particularly, the inventive use and method exhibits the advantages described in spray application to plants and plant parts. Combinations of at least one compound of formula (I) as herein defined or salts thereof with substances including insecticides, attractants, acaricides, fungicides, nematicides, herbicides, growth regulators, safeners, fertlizers, substances which influence plant maturity, and bactericides can likewise be employed in the control of plant disorders in the context of the present invention. In addition, the combined use of at least one compound of formula (I) as herein defined or salts thereof with genetically modified cultivars with a view to increased the control of coffee rust, *citrus* black spot, *citrus* scab or banana black sigatoka disease, is likewise possible.

The following list of fungicides in combination with which the compounds according to the invention can be used is intended to illustrate the possible combinations, but not to impose any limitation: The active ingredients specified herein by their Common Name are known and described, for example, in The Pesticide Manual (16th Ed. British Crop Protection Council) or can be searched in the internet (e.g. www.alanwood.net/pesticides).

Where a compound (A) or a compound (B) can be present in tautomeric form, such a compound is understood herein above and herein below also to include, where applicable, corresponding tautomeric forms, even when these are not specifically mentioned in each case.

All named mixing partners of the classes (1) to (15) can, if their functional groups enable this, optionally form salts with suitable bases or acids.

1) Inhibitors of the ergosterol biosynthesis, for example (1.001) aldimorph, (1.002) azaconazole, (1.003) bitertanol, (1.004) bromuconazole, (1.005) cyproconazole, (1.006) diclobutrazole, (1.007) difenoconazole, (1.008) diniconazole, (1.009) diniconazole-M, (1.010) dodemorph, (1.011) dodemorph acetate, (1.012) epoxiconazole, (1.013) etaconazole, (1.014) fenarimol, (1.015) fenbuconazole, (1.016) fenhexamid, (1.017) fenpropidin, (1.018) fenpropimorph, (1.019) fluquinconazole, (1.020) flurprimidol, (1.021) flusilazole, (1.022) flutriafol, (1.023) furconazole, (1.024) furconazole-cis, (1.025) hexaconazole, (1.026) imazalil, (1.027) imazalil sulfate, (1.028) imibenconazole, (1.029) ipconazole, (1.030) metconazole, (1.031) myclobutanil, (1.032) naftifine, (1.033) nuarimol, (1.034) oxpoconazole, (1.035) paclobutrazol, (1.036) pefurazoate, (1.037) penconazole, (1.038) piperalin, (1.039) prochloraz, (1.040) propiconazole, (1.041) prothioconazole, (1.042) pyributicarb, (1.043) pyrifenox, (1.044) quinconazole, (1.045) simeconazole, (1.046) spiroxamine, (1.047) tebuconazole, (1.048) terbinafine, (1.049) tetraconazole, (1.050) triadimefon, (1.051) triadimenol, (1.052) tridemorph, (1.053) triflumizole, (1.054) triforine, (1.055) triticonazole, (1.056) uniconazole, (1.057) uniconazole-p, (1.058) viniconazole, (1.059) voriconazole, (1.060) 1-(4-chlorophenyl)-2-(1H-1,2,4-triazol-1-yl)cycloheptanol, (1.061) methyl 1-(2,2-dimethyl-2,3-dihydro-1H-inden-1-yl)-1H-imidazole-5-carboxylate, (1.062) N'-{5-(difluoromethyl)-2-methyl-4-[3-(trimethylsilyl)propoxy]phenyl}-N-ethyl-N-methylimidoformamide, (1.063) N-ethyl-N-methyl-N'-{2-methyl-5-(trifluoromethyl)-4-[3-(trimethylsilyl)propoxy]phenyl}imidoformamide, (1.064) O-[1-(4-methoxyphenoxy)-3,3-dimethylbutan-2-yl] 1H-imidazole-1-carbothioate, (1.065) Pyrisoxazole, (1.066) 2-{[3-(2-chlorophenyl)-2-(2,4-difluorophenyl)oxiran-2-yl]methyl}-2,4-dihydro-3H-1,2,4-triazole-3-thione, (1.067) 1-{[3-(2-chlorophenyl)-2-(2,4-difluorophenyl)oxiran-2-yl]methyl}-1H-1,2,4-triazol-5-yl thiocyanate, (1.068) 5-(allylsulfanyl)-1-{[3-(2-chlorophenyl)-2-(2,4-difluorophenyl)oxiran-2-yl]methyl}-1H-1,2,4-triazole, (1.069) 2-[1-(2,4-dichlorophenyl)-5-hydroxy-2,6,6-trimethylheptan-4-yl]-2,4-dihydro-3H-1,2,4-triazole-3-thione, (1.070) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.071) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.072) 1-{[rel(2R,3S)-3-(2-chlorophenyl)-2-(2,4-difluorophenyl)oxiran-2-yl]methyl}-1H-1,2,4-triazol-5-yl thiocyanate, (1.073) 1-{[rel(2R,3R)-3-(2-chlorophenyl)-2-(2,4-difluorophenyl)oxiran-2-yl]methyl}-1H-1,2,4-triazol-5-yl thiocyanate, (1.074) 5-(allylsulfanyl)-1-{[rel(2R,3S)-3-(2-chlorophenyl)-2-(2,4-difluorophenyl)oxiran-2-yl]methyl}-1H-1,2,4-triazole, (1.075) 5-(allylsulfanyl)-1-{[rel(2R,3R)-3-(2-chlorophenyl)-2-(2,4-difluorophenyl)oxiran-2-yl]methyl}-1H-1,2,4-triazole, (1.076) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.077) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.078) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.079) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.080) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.081) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.082) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.083) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.084) 2-[4-(4-chlorophenoxy)-2-(trifluoromethyl)phenyl]-1-(1H-1,2,4-triazol-1-yl)propan-2-ol, (1.085) 2-[4-(4-chlorophenoxy)-2-(trifluoromethyl)phenyl]-1-(1H-1,2,4-triazol-1-yl)butan-2-ol, (1.086) 2-[4-(4-chlorophenoxy)-2-(trifluoromethyl)phenyl]-1-(1H-1,2,4-triazol-1-yl)pentan-2-ol, (1.087) 2-[2-chloro-4-(4-chlorophenoxy)phenyl]-1-(1H-1,2,4-triazol-1-yl)butan-2-ol, (1.088) 2-[2-chloro-4-(2,4-dichlorophenoxy)phenyl]-1-(1H-1,2,4-triazol-1-yl)propan-2-ol, (1.089) (2R)-2-(1-chlorocyclopropyl)-4-[(1R)-2,2-dichlorocyclopropyl]-1-(1H-1,2,4-triazol-1-yl)butan-2-ol, (1.090) (2R)-2-(1-chlorocyclopropyl)-4-[(1S)-2,2-dichlorocyclopropyl]-1-(1H-1,2,4-triazol-1-yl)butan-2-ol, (1.091) (2S)-2-(1-chlorocyclopropyl)-4-[(1S)-2,2-dichlorocyclopropyl]-1-(1H-1,2,4-triazol-1-yl)butan-2-ol, (1.092) (2S)-2-(1-chlorocyclopropyl)-4-[(1R)-2,2-dichlorocyclopropyl]-1-(1H-1,2,4-triazol-1-yl)butan-2-ol, (1.093) (1S,2R,5R)-5-(4-chlorobenzyl)-2-(chloromethyl)-2-methyl-1-(1H-1,2,4-triazol-1-ylmethyl)cyclopentanol, (1.094) (1R,2S,5S)-5-(4-chlorobenzyl)-2-(chloromethyl)-2-methyl-1-(1H-1,2,4-triazol-1-ylmethyl)cyclopentanol, (1.095) 5-(4-chlorobenzyl)-2-(chloromethyl)-2-methyl-1-(1H-1,2,4-triazol-1-ylmethyl)cyclopentanol, (1.096) (2R)-2-[4-(4-chlorophenoxy)-2-(trifluoromethyl)phenyl]-1-(1H-1,2,4-triazol-1-yl)propan-2-ol, (1.097) (2S)-2-[4-(4-chlorophenoxy)-2-(trifluoromethyl)phenyl]-1-(1H-1,2,4-triazol-1-yl)propan-2-ol, (1.098) 1-({(2R,4S)-2-[2-chloro-4-(4-chlorophenoxy)phenyl]-4-methyl-1,3-dioxolan-2-yl}methyl)-1H-1,2,4-triazole, (1.099) 1-({(2S,4S)-2-[2-chloro-4-(4-chlorophenoxy)phenyl]-4-methyl-1,3-dioxolan-2-yl}methyl)-1H-1,2,4-triazole, (1.100) fenpyrazamine, (1.101) N'-(4-{[3-(4-chlorobenzyl)-1,2,4-thiadiazol-5-yl]oxy}-2,5-dimethylphenyl)-N-ethyl-N-methylimidoformamide, (1.102) N'-{4-[(3-tert-butyl-4-cyano-1,2-thiazol-5-yl)oxy]-2-chloro-5-methylphenyl}-N-ethyl-N-methylimidoformamide, (1.103) [3-(4-chloro-2-fluorophenyl)-5-(2,4-difluorophenyl)-1,2-oxazol-4-yl](pyridin-3-yl)methanol, (1.104) (S)-[3-(4-chloro-2-fluorophenyl)-5-(2,4-difluorophenyl)-1,2-oxazol-4-yl](pyridin-3-yl)methanol, (1.105) (R)-[3-(4-chloro-2-fluorophenyl)-5-(2,4-difluorophenyl)-1,2-oxazol-4-yl](pyridin-3-yl)methanol, (1.106) N'-[5-bromo-6-(2,3-dihydro-1H-inden-2-yloxy)-2-methylpyridin-3-yl]-N-ethyl-N-methylimidoformamide, (1.107) N'-{5-bromo-6-[1-(3,5-difluorophenyl)ethoxy]-2-methylpyridin-3-yl}-N-ethyl-N-methylimidoformamide, (1.108) N'-{5-bromo-6-[(1R)-1-(3,5-difluorophenyl)ethoxy]-2-methylpyridin-3-yl}-N-ethyl-N-methylimidoformamide, (1.109) N'-{5-bromo-6-[(1S)-1-(3,5-difluorophenyl)ethoxy]-2-methylpyridin-3-yl}-N-ethyl-N-methylimidoformamide, (1.110) N'-{5-bromo-6-[(cis-4-isopropylcyclohexyl)oxy]-2-methylpyridin-3-yl}-N-ethyl-N-methylimidoformamide, (1.111) N'-{5-bromo-6-[(trans-4-isopropylcyclohexyl)oxy]-2-methylpyridin-3-yl}-N-ethyl-N-methylimidoformamide, (1.112) N'-(2,5-dimethyl-4-phenoxyphenyl)-N-ethyl-N-methylimidoformamide, (1.113) N'-{4-[(4,5-dichloro-1,3-thiazol-2-yl)oxy]-2,5-dimethylphenyl}-N-ethyl-N-methylimidoformamide, (1.114) N'-(4-{3-[(difluoromethyl)sulfanyl]phenoxy}-2,5-dimethylphenyl)-N-ethyl-N-methylimidoformamide, (1.115) N'-(2,5-dimethyl-4-{3-[(1,1,2,2-tetrafluoroethyl)sulfanyl]phenoxy}phenyl)-N-ethyl-N-methylimidoformamide, (1.116) N'-(2,5-dimethyl-4-{3-[(2,2,2-trifluoroethyl)sulfanyl]phenoxy}phenyl)-N-ethyl-N- methylimidoformamide, (1.117) N'-(2,5-dimethyl-4-{3-[(2,2,3,3-tetrafluoropropyl)sulfanyl]phenoxy}phenyl)-N-ethyl-N-methylimidoformamide, (1.118) N'-(2,5-dimethyl-4-{3-[(pentafluoroethyl)sulfanyl]phenoxy}phenyl)-N-ethyl-N-methylimidoformamide, (1.119) N'-(4-{[3-(difluoromethoxy)phenyl]sulfanyl}-2,5-dimethylphenyl)-N-ethyl-N-methylimidoformamide, (1.120) N'-(2,5-dimethyl-4-{[3-(1,1,2,2-tetrafluoroethoxy)phenyl]sulfanyl}phenyl)-N-ethyl-N-methylimidoformamide, (1.121) N'-(2,5-dimethyl-4-{[3-(2,2,2-trifluoroethoxy)phenyl]sulfanyl}phenyl)-N-ethyl-N-methylimidoformamide, (1.122) N'-(2,5-dimethyl-4-{[3-(2,2,3,3-tetrafluoropropoxy)phenyl]sulfanyl}phenyl)-N-ethyl-N-methylimidoformamide, (1.123) N'-(2,5-dimethyl-4-{[3-(pentafluoroethoxy)phenyl]sulfanyl}phenyl)-N-ethyl-N-methylimidoformamide.

2) Inhibitors of the respiratory chain at complex I or II, for example (2.001) bixafen, (2.002) boscalid, (2.003) carboxin, (2.004) diflumetorim, (2.005) fenfuram, (2.006) fluopyram, (2.007) flutolanil, (2.008) fluxapyroxad, (2.009) furametpyr, (2.010) furmecyclox, (2.011) isopyrazam (mixture of syn-epimeric racemate 1RS,4SR,9RS and anti-epimeric racemate 1RS,4SR,9SR), (2.012) isopyrazam (anti-epimeric racemate 1RS,4SR,9SR), (2.013) isopyrazam (anti-epimeric enantiomer 1R,4S,9S), (2.014) isopyrazam (anti-epimeric enantiomer 1S,4R,9R), (2.015) isopyrazam (syn-epimeric racemate 1RS,4SR,9RS), (2.016) isopyrazam (syn-epimeric enantiomer 1R,4S,9R), (2.017) isopyrazam (syn-epimeric enantiomer 1S,4R,9S), (2.018) mepronil, (2.019) oxycarboxin, (2.020) penflufen, (2.021) penthiopyrad, (2.022) sedaxane, (2.023) thifluzamide, (2.024) 1-methyl-N-[2-(1,1,2,2-tetrafluoroethoxy)phenyl]-3-(trifluoromethyl)-1H-pyrazole-4-carboxamide, (2.025) 3-(difluoromethyl)-1-methyl-N-[2-(1,1,2,2-tetrafluoroethoxy)phenyl]-1H-pyrazole-4-carboxamide, (2.026) 3-(difluoromethyl)-N-[4-fluoro-2-(1,1,2,3,3,3-hexafluoropropoxy)phenyl]-1-methyl-1H-pyrazole-4-carboxamide, (2.027) N-[1-(2,4-dichlorophenyl)-1-methoxypropan-2-yl]-3-(difluoromethyl)-1-methyl-1H-pyrazole-4-carboxamide, (2.028) 5,8-difluoro-N-[2-(2-fluoro-4-{[4-(trifluoromethyl)pyridin-2-yl]oxy}phenyl)ethyl]quinazolin-4-amine, (2.029) benzovindiflupyr, (2.030) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.031) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.032) 3-(difluoromethyl)-1-methyl-N-(1,1,3-trimethyl-2,3-dihydro-1H-inden-4-yl)-1H-pyrazole-4-carboxamide, (2.033) 1,3,5-trimethyl-N-(1,1,3-trimethyl-2,3-dihydro-1H-inden-4-yl)-1H-pyrazole-4-carboxamide, (2.034) 1-methyl-3-(trifluoromethyl)-N-(1,1,3-trimethyl-2,3-dihydro-1H-inden-4-yl)-1H-pyrazole-4-carboxamide, (2.035) 1-methyl-3-(trifluoromethyl)-N-[(3R)-1,1,3-trimethyl-2,3-dihydro-1H-inden-4-yl]-1H-pyrazole-4-carboxamide, (2.036) 1-methyl-3-(trifluoromethyl)-N-[(3S)-1,1,3-trimethyl-2,3-dihydro-1H-inden-4-yl]-1H-pyrazole-4-carboxamide, (2.037) 3-(difluoromethyl)-1-methyl-N-[(3S)-1,1,3-trimethyl-2,3-dihydro-1H-inden-4-yl]-1H-pyrazole-4-carboxamide, (2.038) 3-(difluoromethyl)-1-methyl-N-[(3R)-1,1,3-trimethyl-2,3-dihydro-1H-inden-4-yl]-1H-pyrazole-4-carboxamide, (2.039) 1,3,5-trimethyl-N-[(3R)-1,1,3-trimethyl-2,3-dihydro-1H-inden-4-yl]-1H-pyrazole-4-carboxamide, (2.040) 1,3,5-trimethyl-N-[(3S)-1,1,3-trimethyl-2,3-dihydro-1H-inden-4-yl]-1H-pyrazole-4-carboxamide, (2.041) benodanil, (2.042) 2-chloro-N-(1,1,3-trimethyl-2,3-dihydro-1H-inden-4-yl)pyridine-3-carboxamide, (2.043) Isofetamid, (2.044) 1-methyl-3-(trifluoromethyl)-N-[2'-(trifluoromethyl)biphenyl-2-yl]-1H-pyrazole-4-carboxamide, (2.045) N-(4'-chlorobiphenyl-2-yl)-3-(difluoromethyl)-1-methyl-1H-pyrazole-4-carboxamide, (2.046) N-(2',4'-dichlorobiphenyl-2-yl)-3-(difluoromethyl)-1-methyl-1H-pyrazole-4-carboxamide, (2.047) 3-(difluoromethyl)-1-methyl-N-[4'-(trifluoromethyl)biphenyl-2-yl]-1H-pyrazole-4-carboxamide, (2.048) N-(2',5'-difluorobiphenyl-2-yl)-1-methyl-3-(trifluoromethyl)-1H-pyrazole-4-carboxamide, (2.049) 3-(difluoromethyl)-1-methyl-N-[4'-(prop-1-yn-1-yl)biphenyl-2-yl]-1H-pyrazole-4-carboxamide, (2.050) 5-fluoro-1,3-dimethyl-N-[4'-(prop-1-yn-1-yl)biphenyl-2-yl]-1H-pyrazole-4-carboxamide, (2.051) 2-chloro-N-[4'-(prop-1-yn-1-yl)biphenyl-2-yl]nicotinamide, (2.052) 3-(difluoromethyl)-N-[4'-(3,3-dimethylbut-1-yn-1-yl)biphenyl-2-yl]-1-methyl-1H-pyrazole-4-carboxamide, (2.053) N-[4'-(3,3-dimethylbut-1-yn-1-yl)biphenyl-2-yl]-5-fluoro-1,3-dimethyl-1H-pyrazole-4-carboxamide, (2.054) 3-(difluoromethyl)-N-(4'-ethynylbiphenyl-2-yl)-1-methyl-1H-pyrazole-4-carboxamide, (2.055) N-(4'-ethynylbiphenyl-2-yl)-5-fluoro-1,3-dimethyl-1H-pyrazole-4-carboxamide, (2.056) 2-chloro-N-(4'-ethynylbiphenyl-2-yl)nicotinamide, (2.057) 2-chloro-N-[4'-(3,3-dimethylbut-1-yn-1-yl)biphenyl-2-yl]nicotinamide, (2.058) 4-(difluoromethyl)-2-methyl-N-[4'-(trifluoromethyl)biphenyl-2-yl]-1,3-thiazole-5-carboxamide, (2.059) 5-fluoro-N-[4'-(3-hydroxy-3-methylbut-1-yn-1-yl)biphenyl-2-yl]-1,3-dimethyl-1H-pyrazole-4-carboxamide, (2.060) 2-chloro-N-[4'-(3-hydroxy-3-methylbut-1-yn-1-yl)biphenyl-2-yl]nicotinamide, (2.061) 3-(difluoromethyl)-N-[4'-(3-methoxy-3-methylbut-1-yn-1-yl)biphenyl-2-yl]-1-methyl-1H-pyrazole-4-carboxamide, (2.062) 5-fluoro-N-[4'-(3-methoxy-3-methylbut-1-yn-1-yl)biphenyl-2-yl]-1,3-dimethyl-1H-pyrazole-4-carboxamide, (2.063) 2-chloro-N-[4'-(3-methoxy-3-methylbut-1-yn-1-yl)biphenyl-2-yl]nicotinamide, (2.064) 1,3-dimethyl-N-(1,1,3-trimethyl-2,3-dihydro-1H-inden-4-yl)-1H-pyrazole-4-carboxamide, (2.065) 1,3-dimethyl-N-[(3R)-1,1,3-trimethyl-2,3-dihydro-1H-inden-4-yl]-1H-pyrazole-4-carboxamide, (2.066) 1,3-dimethyl-N-[(3S)-1,1,3-trimethyl-2,3-dihydro-1H-inden-4-yl]-1H-pyrazole-4-carboxamide, (2.067) 3-(difluoromethyl)-N-methoxy-1-methyl-N-[1-(2,4,6-trichlorophenyl)propan-2-yl]-1H-pyrazole-4-carboxamide, (2.068) 3-(difluoromethyl)-N-(7-fluoro-1,1,3-trimethyl-2,3-dihydro-1H-inden-4-yl)-1-methyl-1H-pyrazole-4-carboxamide, (2.069) 3-(difluoromethyl)-N-[(3R)-7-fluoro-1,1,3-trimethyl-2,3-dihydro-1H-inden-4-yl]-1-methyl-1H-pyrazole-4-carboxamide, (2.070) 3-(difluoromethyl)-N-[(3S)-7-fluoro-1,1,3-trimethyl-2,3-dihydro-1H-inden-4-yl]-1-methyl-1H-pyrazole-4-carboxamide, (2.071) Pyraziflumid, (2.072) 2-fluoro-6-(trifluoromethyl)-N-(1,1,3-trimethyl-2,3-dihydro-1H-inden-4-yl)benzamide, (2.073) N-cyclopropyl-3-(difluoromethyl)-5-fluoro-N-(2-isopropylbenzyl)-1-methyl-1H-pyrazole-4-carboxamide, (2.074) N-cyclopropyl-N-(2-cyclopropylbenzyl)-3-(difluoromethyl)-5-fluoro-1-methyl-1H-pyrazole-4-carboxamide, (2.075) N-(2-tert-butylbenzyl)-N-cyclopropyl-3-(difluoromethyl)-5-fluoro-1-methyl-1H-pyrazole-4-carboxamide, (2.076) N-(5-chloro-2-ethylbenzyl)-N-cyclopropyl-3-(difluoromethyl)-5-fluoro-1-methyl-1H-pyrazole-4-carboxamide, (2.077) N-(5-chloro-2-isopropylbenzyl)-N-cyclopropyl-3-(difluoromethyl)-5-fluoro-1-methyl-1H-pyrazole-4-carboxamide, (2.078) N-cyclopropyl-3-(difluoromethyl)-N-(2-ethyl-5-fluorobenzyl)-5-fluoro-1-methyl-1H-pyrazole-4-carboxamide, (2.079) N-cyclopropyl-3-(difluoromethyl)-5-fluoro-N-(5-fluoro-2-isopropylbenzyl)-1-methyl-1H-pyrazole-4-carboxamide, (2.080) N-cyclopropyl-N-(2- cyclopropyl-5-fluorobenzyl)-3-(difluoromethyl)-5-fluoro-1-methyl-1H-pyrazole-4-carboxamide, (2.081) N-(2-cyclopentyl-5-fluorobenzyl)-N-cyclopropyl-3-(difluoromethyl)-5-fluoro-1-methyl-1H-pyrazole-4-carboxamide, (2.082) N-cyclopropyl-3-(difluoromethyl)-5-fluoro-N-(2-fluoro-6-isopropylbenzyl)-1-methyl-1H-pyrazole-4-carboxamide, (2.083) N-cyclopropyl-3-(difluoromethyl)-N-(2-ethyl-5-methylbenzyl)-5-fluoro-1-methyl-1H-pyrazole-4-carboxamide, (2.084) N-cyclopropyl-3-(difluoromethyl)-5-fluoro-N-(2-isopropyl-5-methylbenzyl)-1-methyl-1H-pyrazole-4-carboxamide, (2.085) N-cyclopropyl-N-(2-cyclopropyl-5-methylbenzyl)-3-(difluoromethyl)-5-fluoro-1-methyl-1H-pyrazole-4-carboxamide, (2.086) N-(2-tert-butyl-5-methylbenzyl)-N-cyclopropyl-3-(difluoromethyl)-5-fluoro-1-methyl-1H-pyrazole-4-carboxamide, (2.087) N-[5-chloro-2-(trifluoromethyl)benzyl]-N-cyclopropyl-3-(difluoromethyl)-5-fluoro-1-methyl-1H-pyrazole-4-carboxamide, (2.088) N-cyclopropyl-3-(difluoromethyl)-5-fluoro-1-methyl-N-[5-methyl-2-(trifluoromethyl)benzyl]-1H-pyrazole-4-carboxamide, (2.089) N-[2-chloro-6-(trifluoromethyl)benzyl]-N-cyclopropyl-3-(difluoromethyl)-5-fluoro-1-methyl-1H-pyrazole-4-carboxamide, (2.090) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.091) N-cyclopropyl-3-(difluoromethyl)-N-(2-ethyl-4,5-dimethylbenzyl)-5-fluoro-1-methyl-1H-pyrazole-4-carboxamide, (2.092) N-cyclopropyl-3-(difluoromethyl)-5-fluoro-N-(2-isopropylbenzyl)-1-methyl-1H-pyrazole-4-carbothioamide.

3) Inhibitors of the respiratory chain at complex III, for example (3.001) ametoctradin, (3.002) amisulbrom, (3.003) azoxystrobin, (3.004) cyazofamid, (3.005) coumethoxystrobin, (3.006) coumoxystrobin, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) pyribencarb, (3.021) triclopyricarb, (3.022) trifloxystrobin, (3.023) (2E)-2-(2-{[6-(3-chloro-2-methylphenoxy)-5-fluoropyrimidin-4-yl]oxy}phenyl)-2-(methoxyimino)-N-methylacetamide, (3.024) (2E)-2-(methoxyimino)-N-methyl-2-(2-{[({(1E)-1-[3-(trifluoromethyl)phenyl]ethylidene}amino)oxy]methyl}phenyl)acetamide, (3.025) (2E)-2-(methoxyimino)-N-methyl-2-{2-[(E)-({1-[3-(trifluoromethyl)phenyl]ethoxy}imino)methyl]phenyl}acetamide, (3.026) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.027) Fenaminostrobin, (3.028) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.029) methyl (2E)-2-{2-[({cyclopropyl[(4-methoxyphenyl)imino]methyl}sulfanyl)methyl]phenyl}-3-methoxyacrylate, (3.030) N-(3-ethyl-3,5,5-trimethylcyclohexyl)-3-formamido-2-hydroxybenzamide, (3.031) 2-{2-[(2,5-dimethylphenoxy)methyl]phenyl}-2-methoxy-N-methylacetamide, (3.032) (2R)-2-{2-[(2,5-dimethylphenoxy)methyl]phenyl}-2-methoxy-N-methylacetamide, (3.033) (2E,3Z)-5-{[1-(4-chlorophenyl)-1H-pyrazol-3-yl]oxy}-2-(methoxyimino)-N,3-dimethylpent-3-enamide, (3.034) (2S)-2-{2-[(2,5-dimethylphenoxy)methyl]phenyl}-2-methoxy-N-methylacetamide, (3.035) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate.

4) Inhibitors of the mitosis and cell division, for example (4.001) benomyl, (4.002) carbendazim, (4.003) chlorfenazole, (4.004) diethofencarb, (4.005) ethaboxam, (4.006) fluopicolide, (4.007) fuberidazole, (4.008) pencycuron, (4.009) thiabendazole, (4.010) thiophanate-methyl, (4.011) thiophanate, (4.012) zoxamide, (4.013) 5-chloro-7-(4-methylpiperidin-1-yl)-6-(2,4,6-trifluorophenyl)[1,2,4]triazolo[1,5-a]pyrimidine, (4.014) 3-chloro-5-(6-chloropyridin-3-yl)-6-methyl-4-(2,4,6-trifluorophenyl)pyridazine, (4.015) 3-chloro-5-(4-chlorophenyl)-4-(2,6-difluorophenyl)-6-methylpyridazine, (4.016) 4-(4-chlorophenyl)-5-(2,6-difluorophenyl)-3,6-dimethylpyridazine, (4.017) N-[(5-bromo-3-chloropyridin-2-yl)methyl]-2,4-dichloronicotinamide, (4.018) N-[1-(5-bromo-3-chloropyridin-2-yl)ethyl]-2,4-dichloronicotinamide, (4.019) N-[1-(5-bromo-3-chloropyridin-2-yl)ethyl]-2-fluoro-4-iodonicotinamide, (4.020) N-(4-chloro-2,6-difluorophenyl)-4-(2-chloro-4-fluorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(2-chloro-4-fluorophenyl)-N-(2,6-difluorophenyl)-1,3-dimethyl-1H-pyrazol-5-amine, (4.023) 4-(2-chloro-4-fluorophenyl)-N-(2-chloro-6-fluorophenyl)-1,3-dimethyl-1H-pyrazol-5-amine, (4.024) 4-(2-bromo-4-fluorophenyl)-N-(2-chloro-6-fluorophenyl)-1,3-dimethyl-1H-pyrazol-5-amine, (4.025) N-(2-bromo-6-fluorophenyl)-4-(2-chloro-4-fluorophenyl)-1,3-dimethyl-1H-pyrazol-5-amine, (4.026) 4-(2-bromo-4-fluorophenyl)-N-(2-bromophenyl)-1,3-dimethyl-1H-pyrazol-5-amine, (4.027) 4-(2-bromo-4-fluorophenyl)-N-(2-bromo-6-fluorophenyl)-1,3-dimethyl-1H-pyrazol-5-amine, (4.028) 4-(2-bromo-4-fluorophenyl)-N-(2-chlorophenyl)-1,3-dimethyl-1H-pyrazol-5-amine, (4.029) N-(2-bromophenyl)-4-(2-chloro-4-fluorophenyl)-1,3-dimethyl-1H-pyrazol-5-amine, (4.030) 4-(2-chloro-4-fluorophenyl)-N-(2-chlorophenyl)-1,3-dimethyl-1H-pyrazol-5-amine, (4.031) 4-(2-bromo-4-fluorophenyl)-N-(2,6-difluorophenyl)-1,3-dimethyl-1H-pyrazol-5-amine, (4.032) 4-(2-bromo-4-fluorophenyl)-N-(2-fluorophenyl)-1,3-dimethyl-1H-pyrazol-5-amine, (4.033) 3-chloro-4-(2,6-difluorophenyl)-6-methyl-5-phenylpyridazine.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dichlofluanid, (5.011) dithianon, (5.012) dodine, (5.013) dodine free base, (5.014) ferbam, (5.015) fluorofolpet, (5.016) folpet, (5.017) guazatine, (5.018) guazatine acetate, (5.019) iminoctadine, (5.020) iminoctadine albesilate, (5.021) iminoctadine triacetate, (5.022) mancopper, (5.023) mancozeb, (5.024) maneb, (5.025) metiram, (5.026) metiram zinc, (5.027) oxine-copper, (5.028) propamidine, (5.029) propineb, (5.030) sulfur and sulfur preparations including calcium polysulfide, (5.031) thiram, (5.032) tolylfluanid, (5.033) zineb, (5.034) ziram, (5.035) anilazine.

6) Compounds capable to induce a host defence, for example (6.001) acibenzolar-S-methyl, (6.002) isotianil, (6.003) probenazole, (6.004) tiadinil, (6.005) laminarin.

7) Inhibitors of the amino acid and/or protein biosynthesis, for example (7.001) andoprim, (7.002) blasticidin-S, (7.003) cyprodinil, (7.004) kasugamycin, (7.005) kasugamycin hydrochloride hydrate, (7.006) mepanipyrim, (7.007) pyrimethanil, (7.008) 3-(5-fluoro-3,3,4,4-tetramethyl-3,4-dihydroisoquinolin-1-yl)quinoline, (7.009) oxytetracycline, (7.010) streptomycin.

8) Inhibitors of the ATP production, for example (8.001) fentin acetate, (8.002) fentin chloride, (8.003) fentin hydroxide, (8.004) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) polyoxins, (9.007) polyoxorim, (9.008) validamycin A, (9.009) valifenalate, (9.010) polyoxin B, (9.011) (2E)-3-(4-tert-butylphenyl)-3-(2-chloropyridin-4-yl)-1-(morpholin-4-yl)prop-2-en-1-one, (9.012) (2Z)-3-(4-tert-butylphenyl)-3-(2-chloropyridin-4-yl)-1-(morpholin-4-yl)prop-2-en-1-one, (9.013) pyrimorph.

10) Inhibitors of the lipid and membrane synthesis, for example (10.001) biphenyl, (10.002) chloroneb, (10.003) dicloran, (10.004) edifenphos, (10.005) etridiazole, (10.006) iodocarb, (10.007) iprobenfos, (10.008) isoprothiolane, (10.009) propamocarb, (10.010) propamocarb hydrochloride, (10.011) prothiocarb, (10.012) pyrazophos, (10.013) quintozene, (10.014) tecnazene, (10.015) tolclofos-methyl.

11) Inhibitors of the melanin biosynthesis, for example (11.001) carpropamid, (11.002) diclocymet, (11.003) fenoxanil, (11.004) phthalide, (11.005) pyroquilon, (11.006) tricyclazole, (11.007) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) bupirimate, (12.004) clozylacon, (12.005) dimethirimol, (12.006) ethirimol, (12.007) furalaxyl, (12.008) hymexazol, (12.009) metalaxyl, (12.010) metalaxyl-M (mefenoxam), (12.011) ofurace, (12.012) oxadixyl, (12.013) oxolinic acid, (12.014) octhilinone.

13) Inhibitors of the signal transduction, for example (13.001) chlozolinate, (13.002) fenpiclonil, (13.003) fludioxonil, (13.004) iprodione, (13.005) procymidone, (13.006) quinoxyfen, (13.007) vinclozolin, (13.008) proquinazid.

14) Compounds capable to act as an uncoupler, for example (14.001) binapacryl, (14.002) dinocap, (14.003) ferimzone, (14.004) fluazinam, (14.005) meptyldinocap.

15) Further compounds, for example (15.001) benthiazole, (15.002) bethoxazin, (15.003) capsimycin, (15.004) carvone, (15.005) chinomethionat, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezine, (15.015) difenzoquat, (15.016) difenzoquat metilsulfate, (15.017) diphenylamine, (15.018) ecomate, (15.019) flumetover, (15.020) fluoroimide, (15.021) flusulfamide, (15.022) flutianil, (15.023) fosetyl-aluminium, (15.024) fosetyl-calcium, (15.025) fosetyl-sodium, (15.026) hexachlorobenzene, (15.027) irumamycin, (15.028) methasulfocarb, (15.029) methyl isothiocyanate, (15.030) metrafenone, (15.031) mildiomycin, (15.032) natamycin, (15.033) nickel dimethyldithiocarbamate, (15.034) nitrothal-isopropyl, (15.035) oxamocarb, (15.036) oxyfenthiin, (15.037) pentachlorophenol and salts, (15.038) phenothrin, (15.039) phosphorous acid and its salts, (15.040) propamocarb-fosetylate, (15.041) propanosine-sodium, (15.042) pyrrolnitrine, (15.043) tebufloquin, (15.044) tecloftalam, (15.045) tolnifanide, (15.046) triazoxide, (15.047) trichlamide, (15.048) zarilamid, (15.049) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.050) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.051) Oxathiapiprolin, (15.052) 1-(4-methoxyphenoxy)-3,3-dimethylbutan-2-yl 1H-imidazole-1-carboxylate, (15.053) 2,3,5,6-tetrachloro-4-(methylsulfonyl)pyridine, (15.054) 2,3-dibutyl-6-chlorothieno[2,3-d]pyrimidin-4(3H)-one, (15.055) 2,6-dimethyl-1H,5H-[1,4]dithiino[2,3-c:5,6-c']dipyrrole-1,3,5,7(2H,6H)-tetrone, (15.056) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.057) 2-[5-methyl-3-(trifluoromethyl)-1H-pyrazol-1-yl]-1-(4-{4-[(5 S)-5-phenyl-4,5-dihydro-1,2-oxazol-3-yl]-1,3-thiazol-2-yl}piperidin-1-yl)ethanone, (15.058) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.059) 2-butoxy-6-iodo-3-propyl-4H-chromen-4-one, (15.060) 2-chloro-5-[2-chloro-1-(2,6-difluoro-4-methoxyphenyl)-4-methyl-1H-imidazol-5-yl]pyridine, (15.061) 2-phenylphenol and salts, (15.062) 3-(4,4,5-trifluoro-3,3-dimethyl-3,4-dihydroisoquinolin-1-yl)quinoline, (15.063) 3,4,5-trichloropyridine-2,6-dicarbonitrile, (15.064) 5-amino-1,3,4-thiadiazole-2-thiol, (15.065) 5-chloro-N'-phenyl-N'-(prop-2-yn-1-yl)thiophene-2-sulfonohydrazide, (15.066) 5-fluoro-2-[(4-fluorobenzyl)oxy]pyrimidin-4-amine, (15.067) 5-fluoro-2-[(4-methylbenzyl)oxy]pyrimidin-4-amine, (15.068) 5-methyl-6-octyl[1,2,4]triazolo[1,5-a]pyrimidin-7-amine, (15.069) ethyl (2Z)-3-amino-2-cyano-3-phenylacrylate, (15.070) N-(4-chlorobenzyl)-3-[3-methoxy-4-(prop-2-yn-1-yloxy)phenyl]propanamide, (15.071) N-[(4-chlorophenyl)(cyano)methyl]-3-[3-methoxy-4-(prop-2-yn-1-yloxy)phenyl]propanamide, (15.072) N-{(E)-[(cyclopropylmethoxy)imino][6-(difluoromethoxy)-2,3-difluorophenyl]methyl}-2-phenylacetamide, (15.073) N-{(Z)-[(cyclopropylmethoxy)imino][6-(difluoromethoxy)-2,3-difluorophenyl]methyl}-2-phenylacetamide, (15.074) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.075) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.076) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.077) pentyl {6-[({[(1-methyl-1H-tetrazol-5-yl)(phenyl)methylene]amino}oxy)methyl]pyridin-2-yl}carbamate, (15.078) phenazine-1-carboxylic acid, (15.079) quinolin-8-ol, (15.080) quinolin-8-ol sulfate (2:1), (15.081) tert-butyl {6-[({[(1-methyl-1H-tetrazol-5-yl)(phenyl)methylene]amino}oxy)methyl]pyridin-2-yl}carbamate, (15.082) (5-bromo-2-methoxy-4-methylpyridin-3-yl)(2,3,4-trimethoxy-6-methylphenyl)methanone, (15.083) N-[2-(4-{[3-(4-chlorophenyl)prop-2-yn-1-yl]oxy}-3-methoxyphenyl)ethyl]-N2-(methylsulfonyl)valinamide, (15.084) 4-oxo-4-[(2-phenylethyl)amino]butanoic acid, (15.085) but-3-yn-1-yl {6-[({[(Z)-(1-methyl-H-tetrazol-5-yl)(phenyl)methylene]amino}oxy)methyl]pyridin-2-yl}carbamate, (15.086) 4-amino-5-fluoropyrimidin-2-ol (tautomeric form: 4-amino-5-fluoropyrimidin-2(1H)-one), (15.087) propyl 3,4,5-trihydroxybenzoate, (15.088) 2-(6-benzylpyridin-2-yl)quinazoline, (15.089) 2-[6-(3-fluoro-4-methoxyphenyl)-5-methylpyridin-2-yl]quinazoline, (15.090) 3-(4,4-difluoro-3,3-dimethyl-3,4-dihydroisoquinolin-1-yl)quinoline, (15.091) Abscisic acid, (15.092) 9-fluoro-2,2-dimethyl-5-(quinolin-3-yl)-2,3-dihydro-1,4-benzoxazepine, (15.093) 2-{2-fluoro-6-[(8-fluoro-2-methylquinolin-3-yl)oxy]phenyl}propan-2-ol, (15.094) 2-{2-[(7,8-difluoro-2-methylquinolin-3-yl)oxy]-6-fluorophenyl}propan-2-ol, (15.095) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3- thiazol-2-yl)piperidin-1-yl]ethanone, (15.096) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.097) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.098) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.099) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.100) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.101) 2-[3,5-bis(difluoromethyl)-1H-pyrazol-1-yl]-1-[4-(4-{1 (5R)-5-[2-(prop-2-yn-1-yloxy)phenyl]-4,5-dihydro-1,2-oxazol-3-yl}-1,3-thiazol-2-yl)piperidin-1-yl]ethanone, (15.102) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.103) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.104) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.105) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.106) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.107) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.108) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.109) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate.

The present invention further provides a spray solution for treatment of plants, comprising an amount, effective for controlling coffee rust, *citrus* black spot, *citrus* scab or banana black sigatoka disease, of at least one compound of formula (I) as herein defined or salts thereof. The spray solution may comprise other customary constituents, such as solvents, formulation aids, especially water. Further constituents may include active agrochemical ingredients described herein.

The present invention further provides for the use of corresponding spray solutions for increasing the control of coffee rust, *citrus* black spot, *citrus* scab or banana black sigatoka disease. The remarks which follow apply both to the inventive use of at least one compound of formula (I) as herein defined or salts thereof, per se and to the corresponding spray solutions, and to the method of the invention comprising applying said compound, salt thereof, and corresponding spray solutions.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

The compound of the formula (I), or salt thereof, to be used in accordance with the invention can be converted to customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers, and also microencapsulations in polymeric substances. In the context of the present invention, it is especially preferred when 4-phenylbutyric acid or salts thereof, of the formula (I), are used in the form of a spray formulation.

The formulations for spray application are produced in a known manner, for example by mixing the 4-phenylbutyric acid or salts thereof, of the formula (I) with extenders, i.e.

liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are produced either in suitable plants or else before or during application.

The auxiliaries used may be those substances which are suitable for imparting, to the composition itself and/or to preparations derived therefrom (for example spray liquors), particular properties such as particular technical properties and/or else special biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender utilized is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethyl sulfoxide, and also water.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Useful wetting agents which may be present in the formulations usable in accordance with the invention are all substances which promote wetting and which are conventionally used for the formulation of active agrochemical ingredients. Preference is given to using alkyl naphthalenesulfonates, such as diisopropyl or diisobutyl naphthalenesulfonates.

Useful dispersants and/or emulsifiers which may be present in the formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants are especially ethylene oxide/propylene oxide block polymers, alkylphenol polyglycol ethers and tristryrylphenol polyglycol ether, and the phosphated or sulfated derivatives thereof. Suitable anionic dispersants are especially lignosulfonates, polyacrylic acid salts and arylsulfonate/formaldehyde condensates.

Antifoams which may be present in the formulations usable in accordance with the invention are all foam-inhibiting substances conventionally used for the formulation of active agrochemical ingredients. Silicone antifoams and magnesium stearate can be used with preference.

Preservatives which may be present in the formulations usable in accordance with the invention are all substances usable for such purposes in agrochemical compositions. Examples include dichlorophene and benzyl alcohol hemiformal.

Secondary thickeners which may be present in the formulations usable in accordance with the invention are all substances usable for such purposes in agrochemical compositions. Preferred examples include cellulose derivatives, acrylic acid derivatives, xanthan, modified clays and finely divided silica.

Stickers which may be present in the formulations usable in accordance with the invention include all customary binders usable in seed-dressing products. Preferred examples include polyvinylpyrrolidone, polyvinyl acetate, polyvinyl alcohol and tylose. Gibberellins which may be present in the formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schaidlingsbekaimpfungsmittel" [Chemistry of the Crop Protection Compositions and Pesticides], vol. 2, Springer Verlag, 1970, p. 401-412).

Further additives may be fragrances, mineral or vegetable, optionally modified oils, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations contain generally between 0.01 and 98% by weight, preferably between 0.5 and 90%, of the 4-phenylbutyric acid and/or salts thereof, of the formula (I).

The compound of formula (I) as herein defined or salt thereof can be present in commercially available formulations and also in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

The preparation and the use of the inventive compounds is illustrated by the examples which follow.

N-cyclopropyl amides of formula (I) wherein T represents an oxygen atom, can be prepared by condensation of a substituted N-cyclopropyl benzylamine with 3-(difluoromethyl)-5-fluoro-1-methyl-1H-pyrazole-4-carbonyl chloride according to WO-2007/087906 (process P1) and WO-2010/130767 (process P1—step 10).

Substituted N-cyclopropyl benzylamines are known or can be prepared by known processes such as the reductive amination of a substituted aldehyde with cyclopropanamine (*J. Med. Chem.*, 2012, 55 (1), 169-196) or by nucleophilic substitution of a substituted benzyl alkyl (or aryl)sulfonate or a substituted benzyl halide with cyclopropanamine (*Bioorg. Med. Chem.*, 2006, 14, 8506-8518 and WO-2009/140769).

3-(difluoromethyl)-5-fluoro-1-methyl-1H-pyrazole-4-carbonyl chloride can be prepared according to WO-2010/130767 (process P1—steps 9 or 11)

N-cyclopropyl thioamides of formula (I) wherein T represents a sulfur atom, can be prepared by thionation of a N-cyclopropyl amide of formula (I) wherein T represents a oxygen atom, according to WO-2009/016220 (process P1) and WO-2010/130767 (process P3).

The following examples illustrate in a non limiting manner the preparation of the compounds of formula (I) according to the invention.

Preparation of N-cyclopropyl-3-(difluoromethyl)-5-fluoro-N-(2-isopropylbenzyl)-1-methyl-1H-pyrazole-4-carboxamide (Compound A1)

Step A: Preparation of N-(2-isopropylbenzyl)cyclopropanamine

To a solution of 55.5 g (971 mmol) of cyclopropanamine in 900 mL of methanol, are successively added 20 g of 3 Å molecular sieves and 73 g (1.21 mol) of acetic acid. 72 g (486 mmol) of 2-isopropyl-benzaldehyde are then added dropwise and the reaction mixture is further heated at reflux for 4 hours.

The reaction mixture is then cooled to 0° C. and 45.8 g (729 mmol) of sodium cyanoborohydride are added by portion in 10 min and the reaction mixture is stirred again for 3 hours at reflux. The cooled reaction mixture is filtered over a cake of diatomaceous earth. The cake is washed abundantly by methanol and the methanolic extracts are concentrated under vacuum. Water is then added to the residue and the pH is adjusted to 12 with 400 mL of a 1 N aqueous solution of sodium hydroxide. The watery layer is extracted with ethyl acetate, washed by water (2×300 mL) and dried over magnesium sulfate to yield 81.6 g (88%) of N-(2-isopropylbenzyl)cyclopropanamine as a yellow oil used as such in the next step.

The hydrochloride salt can be prepared by dissolving N-(2-isopropylbenzyl)cyclopropanamine in diethyl-ether (1.4 mL/g) at 0° C. followed by addition of a 2 M solution of hydrochloric acid in diethylether (1.05 eq.). After a 2 hours stirring, N-(2-isopropylbenzyl)cyclopropanamine hydrochloride (1:1) is filtered off, washed by diethylether and dried under vacuum at 40° C. for 48 hours. Mp (melting point)=149° C.

Step B: preparation of N-cyclopropyl-3-(difluoromethyl)-5-fluoro-N-(2-isopropylbenzyl)-1-methyl-1H-pyrazole-4-carboxamide To 40.8 g (192 mmol) of N-(2-isopropylbenzyl)cyclopropanamine in 1 L of dry tetrahydrofurane are added at room temperature, 51 mL (366 mmol) of triethylamine. A solution of 39.4 g (174 mmol) of 3-(difluoromethyl)-5-fluoro-1-methyl-1H-pyrazole-4-carbonyl chloride in 800 mL of dry tetrahydrofurane is then added dropwise while maintaining the temperature below 34° C. The reaction mixture is heated at reflux for 2 hours then left overnight at room temperature. Salts are filtered off and the filtrate is concentrated under vacuum to yield 78.7 g of a brown oil. Column chromatography on silica gel (750 g—gradient n-heptane/ethyl acetate) yields 53 g (71% yield) of N-cyclopropyl-3-(difluoromethyl)-5-fluoro-N-(2-isopropylbenzyl)-1-methyl-1H-pyrazole-4-carboxamide as a yellow oil that slowly crystallizes. Mp=76-79° C.

In the same way, compounds A2 to A19 can be prepared according to the preparation described for compound A1.

Preparation of N-cyclopropyl-3-(difluoromethyl)-5-fluoro-N-(2-isopropylbenzyl)-1-methyl-1H-pyrazole-4-carbothioamide (Compound A20)

A solution of 14.6 g (65 mmol) of phosphorus pentasulfide and 48 g (131 mmol) of N-cyclopropyl-3-(difluoromethyl)-5-fluoro-N-(2-isopropylbenzyl)-1-methyl-1H-pyrazole-4-carboxamide in 500 ml of dioxane are heated at 100° C. for 2 hours. 50 ml of water are then added and the reaction mixture is further heated at 100° C. for another hour. The cooled reaction mixture is filtered over a basic alumina cartridge. The cartridge is washed by dichloromethane and the combined organic extracts are dried over magnesium sulfate and concentrated under vacuum to yield 55.3 g of an orange oil. The residue is tritured with a few mL of diethylether until crystallisation occurs. Crystals are filtered off and dried under vacuum at 40° C. for 15 hours to yield 46.8 g (88% yield) of N-cyclopropyl-3-(difluoromethyl)-5-fluoro-N-(2-isopropylbenzyl)-1-methyl-1H-pyrazole-4-carbothioamide. Mp=64-70° C.

Table 1 provides the log P and NMR data ($^1$H) of compounds A1 to A20.

In table 1, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

| Cmpd | logP | NMR |
|---|---|---|
| A1 | 3.35 | $^1$H NMR (500 MHz, CHCl$_3$-d): δ ppm 0.64 (bs, 4H), 1.21 (d, J = 6.60 Hz, 6H), 2.44-2.80 (m, 1H), 3.01-3.29 (m, 1H), 3.78 (s, 3H), 4.76 (bs, 2H), 6.89 (t, J = 54.70 Hz, 1H), 7.12-7.33 (m, 4H). |
| A2 | 3.44 | $^1$H NMR (500 MHz, CHCl$_3$-d): δ ppm 0.47-0.77 (m, 6H), 0.80-1.04 (m, 2H), 1.92 (bs, 1H), 2.66 (bs, 1H), 3.80 (s, 3H), 4.92 (bs, 2H), 6.90 (t, J = 54.50 Hz, 1H), 7.01-7.25 (m, 4H). |
| A3 | 4.06 | $^1$H NMR (500 MHz, CHCl$_3$-d): δ ppm 0.61 (bs, 4H), 1.46 (s, 9H), 2.77-2.98 (m, 1H), 3.89 (s, 3H), 5.05 (bs, 2H), 6.91 (t, J = 54.70 Hz, 1H), 7.20 (bs, 3H), 7.35-7.48 (m, 1H). |
| A4 | 3.76 | $^1$H NMR (300 MHz, CHCl$_3$-d): δ ppm 0.65-0.69 (m, 4H), 1.21 (t, 3H), 2.62-2.64 (m, 3H), 3.81 (s, 3H), 4.70 (s, 2H), 6.85 (t, J = 54.6 Hz, 1H), 7.04-7.22 (m, 3H). |
| A5 | 4.09 | $^1$H NMR (500 MHz, CHCl$_3$-d): δ ppm 0.63-0.73 (m, 4H), 1.22 (d, J = 6.92 Hz, 6H), 2.59-2.87 (m, 1H), 2.98-3.30 (m, 1H), 3.82 (s, 3H), 4.74 (bs, 2H), 6.88 (t, J = 54.40 Hz, 1H), 7.20-7.27 (m, 3H). |
| A6 | 3.41 | $^1$H NMR (300 MHz, CHCl$_3$-d): δ ppm 0.65-0.66 (m, 4H), 1.21 (t, 3H), 2.62 (q, 2H), 2.64 (bs, 1H), 3.81 (s, 3H), 4.71 (s, 2H), 6.86 (t, J = 54.6 Hz, 1H), 6.89-6.95 (m, 2H), 7.13-7.18 (m, 1H). |

-continued

| Cmpd | logP | NMR |
|---|---|---|
| A7 | 3.70 | $^1$H NMR (300 MHz, $CHCl_3$-d): δ ppm 0.65-0.69 (m, 4H), 1.22 (d, 6H), 2.69 (bs, 1H), 3.10-3.14 (m, 1H), 3.81 (s, 3H), 4.75 (s, 2H), 6.86 (t, J = 54.6 Hz, 1H), 6.88-6.93 (m, 2H), 7.23-7.28 (m, 1H). |
| A8 | 3.46 | $^1$H NMR (300 MHz, $CHCl_3$-d): δ ppm 0.60-0.66 (m, 6H), 0.89-0.95 (m, 2H), 1.82-1.84 (m, 1H), 2.73 (bs, 1H), 3.81 (s, 3H), 4.89 (s, 2H), 6.68-6.99 (m, 4H). |
| A9 | 4.21 | $^1$H NMR (300 MHz, $CHCl_3$-d): δ ppm 0.64-0.68 (m, 4H), 1.56-1.62 (m, 2H), 1.62-1.70 (m, 2H), 1.76-1.83 (m, 2H), 1.96-2.05 (m, 2H), 2.71 (bs, 1H), 3.13-3.19 (m, 1H), 3.81 (s, 3H), 4.76 (s, 2H), 6.86 (t, J = 54.0 Hz, 1H), 6.87-6.97 (m, 2H), 7.23-7.28 (m, 1H). |
| A10 | 3.65 | $^1$H NMR (400 MHz, $CHCl_3$-d): δ ppm 0.65 (bs, 4H), 1.21 (d, J = 6.75 Hz, 5H), 2.29-2.59 (m, 1H), 3.00-3.36 (m, 1H), 3.79 (s, 3H), 4.83 (s, 2H), 6.68-7.06 (m, 2H), 7.13 (d, J = 7.78 Hz, 1H), 7.27-7.33 (m, 1H). |
| A11 | 3.70 | $^1$H NMR (500 MHz, $CHCl_3$-d): δ ppm 0.65 (bs, 4H), 2.31 (s, 3H), 2.64 (m, 1H), 3.81 (s, 3H), 4.73 (bs, 2H), 6.89 (t, J = 54.6 Hz, 1H), 7.01-7.14 (m, 3H). |
| A12 | 3.99 | $^1$H NMR (500 MHz, $CHCl_3$-d): δ ppm 0.66 (bs, 4H), 1.22 (d, J = 6.97 Hz, 6H), 2.31 (s, 3H), 2.54-2.75 (m, 1H), 2.99-3.25 (m, 1H), 3.81 (s, 3H), 4.75 (bs, 2H), 6.89 (t, J = 53.90 Hz, 1H), 7.01-7.23 (m, 3H). |
| A13 | 3.76 | $^1$H NMR (500 MHz, $CHCl_3$-d): δ ppm 0.61-0.68 (m, 6H), 0.80-1.00 (m, 2H), 1.74-2.00 (m, 1H), 2.31 (s, 3H), 2.53-2.82 (m, 1H), 3.81 (s, 3H), 4.89 (bs, 2H), 6.83 (t, J = 54.80 Hz, 1H), 6.91-7.06 (m, 3H). |
| A14 | 4.36 | $^1$H NMR (500 MHz, $CHCl_3$-d): δ ppm 0.62 (m, 4H), 1.44 (s, 9H), 2.28 (s, 3H), 2.74-3.02 (m, 1H), 3.83 (bs, 3H), 5.02 (bs, 2H), 6.85 (t, J = 54.40 Hz, 1 H), 7.01 (bs, 1H), 7.21-7.29 (m, 2 H). |
| A15 | 3.80 | $^1$H NMR (500 MHz, $CHCl_3$-d): δ ppm 0.50-0.67 (m, 4H), 2.81 (bs, 1H), 3.78 (s, 3H), 4.85 (bs, 2H), 6.78 (t, J = 55.00 Hz, 1H), 7.20-7.29 (m, 2H), 7.54 (d, J = 8.17 Hz, 1H). |
| A16 | 3.78 | $^1$H NMR (500 MHz, $CHCl_3$-d): δ ppm 0.55-0.70 (m, 4H), 2.37 (s, 3H), 2.72-3.04 (m, 1H), 3.83 (bs, 3H), 4.91 (bs, 2H), 6.86 (t, J = 54.50 Hz, 1H), 7.10-7.20 (m, 2H), 7.54 (d, J = 7.89 Hz, 1H). |
| A17 | 3.46 | $^1$H NMR (500 MHz, $CHCl_3$-d): δ ppm 0.47-0.64 (m, 4H), 2.29-2.55 (m, 1H), 3.80 (s, 3H), 5.05 (s, 2H), 6.95 (t, J = 54.40 Hz, 1H), 7.40 (t, J = 7.86 Hz, 1H), 7.60-7.70 (dd, 2H). |
| A18 | 3.62 | $^1$H NMR (500 MHz, $CHCl_3$-d): δ ppm 0.50-0.74 (m, 4H), 2.45-2.71 (m, 1H), 3.81 (s, 3H), 4.99 (s, 2H), 6.91 (t, J = 54.40 Hz, 1H), 7.45-7.57 (m, 2H). |
| A19 | 4.04 | $^1$H NMR (500 MHz, $CHCl_3$-d): δ ppm 0.65 (bs, 4H), 1.20 (t, J = 7.43 Hz, 3H), 2.22 (s, 3H), 2.24 (s, 3H), 2.58-2.64 (m, 2H), 3.80 (s, 3H), 4.70 (bs, 2H), 6.89 (t, J = 54.70 Hz, 3H), 6.98 (bs, 2H). |
| A20 | 4.36 | $^1$H NMR (500 MHz, $CHCl_3$-d): δ ppm 0.55-0.84 (m, 4H), 1.27 (d, J = 6.97 Hz, 6H), 2.73-2.85 (m, 1H), 3.04-3.23 (m, 1H), 3.80 (s, 3H), 4.60-5.06 (m, 1H), 6.99-7.38 (m, 5H). |

BIOLOGICAL EXAMPLES

1. Control of Rust (*Hemileia vastatrix*) on Coffee Crop (Field Trials).

Four field trials were implemented in Brazil in 2013 and 2014 to evaluate the performance of compounds against *Hemileia vastatrix* on Coffee.

formulation containing 100 g of compound per liter was applied in consecutive foliar sprays at 3 occasions every 30 to 50 days in most of the trials. Spray volumes vary from 400 L to 500 L/Ha.

Assessments were realized on leaves—Data are expressed in % efficacy against rust on leaves compared to untreated plants.

| | Trial(s) | | | | |
|---|---|---|---|---|---|
| Compound (concentration) | 400-300 L/Ha rates active ingredient g a.i./ha | A % Efficacy (Abbott) | B % Efficacy (Abbott) | C % Efficacy (Abbott) | D % Efficacy (Abbott) |
| N-(5-chloro-2-isopropylbenzyl)-N-cyclopropyl-3-(difluoromethyl)-5-fluoro-1-methyl-1H-pyrazole-4-carboxamide (compound A5) (100 g/L) | 50 | 84 | 61 | 95 | 73 |
| Opera (Epoxyconazole + Pyraclostrobin.) | 50 + 133 | | | | 79 |

The trials were carried out according to standard experimental practice to protect the canopy from the rust, responsible to defoliation and then yield losses. A typical fungicide The assessments realized in the four trials reported in the table show the high level of efficacy of compound A5 used in solo at 50 g ai/ha, against coffee rust. The level of efficiency is in the same range than the one obtained with the standard Opera, used at the recommended dose. Nevertheless, compound A5 is able to obtain said high efficiency when it is used in solo, and at the very low dose of 50 g ai/ha, while Opera is a mix of two active ingredient, and used at the high concentration of 183 g a.i./ha (50+133).

Conclusion

The example above demonstrates that compound A5 represents a new alternative tool to control Coffee rust with low active rates of 50 g ai/ha. The efficacy at these low rates competes with already sold ready mix compounds based on mixtures of epoxyconazole and pyraclostrobin (Opera), while said latest mixtures is used at the concentration of 183 g a.i./ha.

Compound A5 has a high and unexpected better efficiency (comparable control at much less rate) than Opera and can participate to the reduction of chemical loading in plantations.

2. Control of Black Spot (*Guignardia citricarpa*) and Scab (*Elsinoe* Spp) on Citrus Crop (Field Trials).

Five field trials were implemented in South Africa, Brazil and Japan in 2013 and 2014 to evaluate the performance of compounds against two main diseases having high effect on marketable yield: *Elsinoe fawcettii* and *Guignardia citricarpa* are hosted by many *citrus* species. Both are able to infest fruits and both are quarantine pathogens limiting the exportation outside of the growing countries. The protection against these two pathogens gives a clear advantage for farmers to be present on the export market.

The trials were carried out according to standard experimental practice to protect the canopy including fruits in each country. A typical fungicide formulation containing 100 g of compound per liter was applied in consecutive foliar sprays at 5 to 6 occasions every month to control black spot and at 1 to 3 occasions every 14 days to control Scab infections. Spray volumes vary from 2000 L to 3000 L/Ha.

Results from the Trials *Guignardia citricarpa* (Black Spot)

| Compound (concentration) | Trial(s) 2000 to 3000 L/Ha rates active ingredient g a.i./100 L | A % Efficacy (Abbott) | B % Efficacy (Abbott) | C % Efficacy (Abbott) |
|---|---|---|---|---|
| N-(5-chloro-2-isopropylbenzyl)-N-cyclopropyl-3-(difluoromethyl)-5-fluoro-1-methyl-1H-pyrazole-4-carboxamide (compound A5) (100 g/L) | 10 | 73 | 72 | 91.3 |
|  | 15 | 70 | 83 | 93.9 |
| Sancozeb (Mancozeb) | 160 | 40 | 35 | — |

The assessments show that compound A5 used at very low rates (from 10 g to 15 g a.i./100 L) gives superior efficacy than Mancozeb currently used to control Black Spot, despite Mancozeb is used as a very higher rate (160 g a.i./100 L). Commercial standard Mancozeb needs significantly higher a.i. concentration (around 15 times higher) to obtain comparable or even lower efficiency.

Results from the Trials *Elsinoe fawcettii* (Scab)

| Compound (concentration) | Trial(s) 3000 L/Ha rates active ingredient g a.i./100 L | A % Efficacy (Abbott) | B % Efficacy (Abbott) |
|---|---|---|---|
| N-(5-chloro-2-isopropylbenzyl)-N-cyclopropyl-3-(difluoromethyl)-5-fluoro-1-methyl-1H-pyrazole-4-carboxamide (compound A5) (100 g/L) | 2.5 | 96 | 92 |
|  | 5 | 95 | 70 |
| Stroby DF (Kresoxim methyl) | 23.5 | 86 | 82 |
| Delan FL (Dithianon) | 400 | 65 | 48 |

The assessments show that compound A5 used at very low rates (from 2.5 g to 5 g ai/100 L) gives superior efficacy than commercial standards Kresoxim methyl and Dithianon currently used to control Black Spot, although said commercial standards are used at very higher rate (around 10 times higher for Stroby DF and around 160 times higher for Dithianon).

Conclusion

The examples above demonstrate that compound A5 brings high level of activity at very low rates (below 15 g ai/ha) to protect significantly *citrus* plantations against quarantine diseases like Black spot and Scab.

The efficacy at these low rates is superior to commercial compounds, although said commercial compounds are used currently at very higher rates: at least 10 times higher (Kresoxim methyl), 15 times higher (Mancozeb) or even 160 times higher (Dithianon). Compound A5 can participate to the reduction of chemical loading in plantations.

3. Control of Black Sigatoka on Banana Crop (Field Trials).

Two field trials were implemented in 2013 in Costa Rica and Philippines to evaluate the performance of compounds against *Mycosphaerella fijiensis* infection on Banana.

A typical fungicide formulation containing 100 g of compound per liter was applied every 7 to 12 days in consecutive foliar sprays. The trials were carried out according to standard experimental practice with spay adjuvant and mineral oil used in tank mix as it is usual on banana plantation in each country.

Data are expressed in Number of healthy leaves present at the end of the trial on each Banana plant (more leaves present mean better quantity and quality of harvest).

Results from the Trials Black Sigatoka—Number of Healthy Leaves Per Plant.

| Composition (concentration) | rates active ingredient g a.i./ha | Trial(s) A Number healthy Leaves 2DAT7 | B Number healthy Leaves 25DAT13 |
|---|---|---|---|
| UNTREATED |  | 8.5 | 8.7 |
| N-(5-chloro-2-isopropylbenzyl)-N-cyclopropyl-3-(difluoromethyl)-5-fluoro-1-methyl-1H-pyrazole-4-carboxamide (compound A5) (100 g/L) | 6.25 | 11.5 | 13.4 |
|  | 12.5 | 12.2 | 14.4 |
|  | 25 | 12 | 16.2 |
| Boscalid 500 g/L | 150 | — | 13.1 |

The assessments show that compound A5 used at very low rates (6.25 g ai/ha) is able to control Black Sigatoka in plantation areas. The average of about +3 leaves per plant gives a significant advantage for further fruit production levels. Registered compound Boscalid needs higher rate (150 g a.i./ha) for equivalent or even lower efficacy measured in the trial.

CONCLUSION

The example above demonstrates that compound A5 represents a new standard for Banana protection with a high level of activity at very low rates, below 25 g ai/ha, to protect significantly plants against Black Sigatoka. The efficacy at these low rates is at least equivalent to already registered compound Boscalid which is used at rates at least 6 to 24 times higher, and can participate to the reduction of chemical loading in plantations.

The invention claimed is:

1. A method for treating plants in need of control of citrus black spot, comprising applying to said plants or parts of said plants, to the seeds from which they grow or to the locus in which they grow, an effective amount for controlling the disease, of N-(5-chloro-2-isopropylbenzyl)-N-cyclopropyl-3-(difluoromethyl)-5-fluoro-1-methyl-1H-pyrazole-4-carboxamide, or an agrochemically acceptable salt thereof, wherein the citrus black spot is caused by *Guignardia citricarpa.*

2. The method according to claim 1, wherein N-(5-chloro-2-isopropylbenzyl)-N-cyclopropyl-3-(difluoromethyl)-5-fluoro-1-methyl-1H-pyrazole-4-carboxamide or an agrochemically acceptable salt thereof, is applied to said plants, to the seeds from which they grow or the locus in which they grow at an application rate of from about 0.001 kg/ha to about 1 kg/ha of N-(5-chloro-2-isopropylbenzyl)-N-cyclopropyl-3-(difluoromethyl)-5-fluoro-1-methyl-1H-pyrazole-4-carboxamide.

3. The method according to claim 1, wherein N-(5-chloro-2-isopropylbenzyl)-N-cyclopropyl-3-(difluoromethyl)-5-fluoro-1-methyl-1H-pyrazole-4-carboxamide, or an agrochemically acceptable salt thereof, is applied by spray application to plants and plant parts in combination with one or more active ingredients selected from the group consisting of insecticides, attractants, acaricides, fungicides, nematicides, herbicides, growth regulators, fertilizers, safeners, substances which influence plant maturity and bactericides.

4. The method according to claim 1, wherein N-(5-chloro-2-isopropylbenzyl)-N-cyclopropyl-3-(difluoromethyl)-5-fluoro-1-methyl-1H-pyrazole-4-carboxamide, or an agrochemically acceptable salt thereof, is applied to genetically modified cultivars, the seed thereof, or to cultivated areas on which these cultivars grow.

* * * * *